(12) United States Patent
Haj-Yousef (10) Patent No.: US 6,359,597 B2
(45) Date of Patent: Mar. 19, 2002

(54) METHOD AND DEVICE FOR DETECTING AND MONITORING CONCEALED BODIES AND OBJECTS

(76) Inventor: Yosri Mohamad Taher Haj-Yousef, Emirates Intellectual Property Services, P.O. Box 29180, Sharjah (AE)

( * ) Notice: Subject to any disclaimer, the term of this patent is extended or adjusted under 35 U.S.C. 154(b) by 0 days.

(21) Appl. No.: 09/882,488

(22) Filed: Jun. 15, 2001

(30) Foreign Application Priority Data

Jul. 3, 2000 (AE) ............................................. 53/2000

(51) Int. Cl.[7] ................................................. H01Q 1/50
(52) U.S. Cl. .................... 343/850; 340/573.1; 600/534; 324/160; 128/204.23
(58) Field of Search ................................ 343/703, 850, 343/852, 860; 340/573.1, 573.4, 573.7; 600/430, 534; 324/160, 163, 165; 128/204.23, 204.21, 204.18

(56) References Cited

U.S. PATENT DOCUMENTS

| 3,599,197 | A | * | 8/1971 | Boyko ........................ 340/258 |
| 4,926,868 | A | * | 5/1990 | Larsen .................... 128/653 R |
| 5,670,886 | A | * | 9/1997 | Wolff et al. ................. 324/644 |
| 6,062,216 | A | * | 5/2000 | Corn ...................... 128/204.23 |
| 6,233,479 | B1 | * | 5/2001 | Haddad et al. ............. 600/430 |

* cited by examiner

Primary Examiner—Tho G. Phan
(74) Attorney, Agent, or Firm—Christensen O'Connor Johnson Kindness PLLC (57) ABSTRACT

A method and a device for non-invasively and remotely detecting or monitoring visible or invisible concealed moving bodies and objects (9) located in scrutinized media (8), by means of tracking the RF impedance match variations between the inspected media which contains the targeted moving object and a stable RF transmitter (1), through surrounding the inspected media with a power field of HF EM-waves, by one or more transmitting antennas (6) made from metallic sheets or wires.

11 Claims, 7 Drawing Sheets

METHOD AND DEVICE FOR DETECTING AND MONITORING CONCEALED BODIES AND OBJECTS

BACKGROUND OF THE INVENTION

The present invention, which has a multi-application usage, generally pertains to a method for non-invasively and remotely sensing of visible and invisible moving bodies or objects, even those hidden in immune barriers and concealed locations.

Detection of movement occurs by tracking any variation in the Radio Frequency (RF) impedance match of a scrutinized media in which the targeted object is located, with a power RF transmitter. ("Media," in the context of these documents, will mean the environment close to the moving body or object under inspection. "Targeted object" will mean the moving body or object under inspection.)

A stable power Electro-Magnetic (EM) field, at a fixed frequency (High range), is created around the targeted object. By extracting the slight power changes from the resultant forward and reflected powers generated within the transmitting line (coaxial cable, dual parallel wires, or strip lines) that transfers and carries the transmitted EM-energy, any movement of the targeted object within the media can be detected.

By way of example and not of limitation, the method of the present invention comprises usage in the following applications:

1. In the agricultural field by a device for detection of early infestation by red palm weevil and tunnel borers in tree trunks and upper roots. This application is particularly important where the insect larvae secretly and silently consume the tree's core, producing tunnels and hollows that lead to the death of the tree.

Detection of early infestation is vital but extremely difficult, and by the time the evidence of presence of the pest becomes apparent, it is too late to save the tree. Unless the infestation is detected and treated at early stage, the life of the tree is limited to a few months.

Present research indicates that this pest seriously threatens untold millions of palm and fruit trees all over the world and unless this problem is effectively resolved very soon, the likelihood is that all trees in afflicted areas will die within a few years.

2. In the medical field, this method can be implemented in various applications, such as a device for real-time monitoring of the heart's motion (kinetocardiograph). There is no direct contact of device circuits to the human body. Data drawn from this method will add new parameters in the field of medicine for more versatile and comprehensive diagnosis of heart problems.

The principal present-day methods for heart monitoring are:

Electrocardiograph (ECG), which monitors the heart activity by tracking the electrical signals generated by the chemical reaction of the heart muscles. This method employs the use of electrodes directly attached to the patient.

Phonocardiogragh (PCG), which audibly indicates the heart motion. This method involves the use of a microphone placed directly on the patient.

Doppler Cardiograph (DCG) monitors the heart activity using the ultrasound Doppler effect. This method employs the use of an ultrasound probe in contact with the patient's body under specific conditions.

All of the foregoing methods are measuring reactions to the heart's motion, and all require direct contact with the patient by electrodes, etc.

The present invention has the following advantages by monitoring the heart:

In real time.

Directly, without dependence on reaction.

Does not require any direct contact with the patient.

Monitors the motion activity of "all" of the components of the heart.

Additionally, the method can also be used as a device for continuous monitoring of newborn, premature babies, and patients under intensive care. All the present-day methods require direct contact with the patient/baby, either in the form of contact electrodes or pressure sensor mattresses, but they are impractical in the case of premature babies, due to the frequent requirement to move the baby for feeding, cleaning, etc.

The device can also be utilized to give an early alarm, whenever a life-threatening situation arises, such as: Sudden Infant Death Syndrome (SIDS), by continuous and precise remote monitoring of the movement of vital organs, such as lungs in the breathing process. This will accelerate emergency intensive care.

Since the device is monitoring the organ activity remotely, it does not require attachment of electrodes etc to the body. The data drawn from this device can also be collated for analytical evaluation for diagnostic purposes.

Non-invasively and remotely monitoring of the human vital signs or body movements are necessary in the following additional circumstances:

Where burn patients cannot tolerate the attachment of electrodes directly to the skin surface.

Where disaster victims are trapped and concealed in building debris following building collapse.

Where it is essential to know and react to the condition of aircraft pilots and astronauts when there is a possibility of temporary "black out" due to extreme maneuvers in flight.

3. This method also will be used to detect sudden instability in flow of liquids, for example, blood through tubes in open-heart surgery and dialysis treatment, by non-invasively sensing the flow intensity of the liquid.

This new method will provide a mechanism to monitor and sense the slightest unexpected change in flow process. This will guarantee, for example, not to have any air bubble leakage into blood path, and at the same time protecting it from thrombosis and contamination, since this is done by non-invasive sensing without any direct contact.

4. Another application will be in concealed security systems for protection against thieves and intruders, through sensing body movements in corridors or regions that need protection. The sensors can be hidden underground or inside or in back of the walls, even cement ones, so that they can not be located and disabled by intruders.

5. Automatic access control is also an area where the method will be effectively used, since most existing automatic outdoor control systems are affected by light/darkness, dust, heat, etc.

Another example is monitoring and controlling traffic and traffic signals by sensing vehicle movements in road traffic activity.

From the necessarily limited examples given above, it will be seen that the method has a very wide spectrum of applications.

SUMMARY OF THE INVENTION

It is an established fact that the optimum transfer of EM-energy from an RF transmitter to the load occurs when the output impedance of the transmitter matches the load impedance.

The popular method used to predict the level of match is achieved by sampling the actual values of the forward and the reflected powers generated within the transmission-line that transfers and carries the transmitted EM-energy, these values can be easily picked up by passing the transmitted RF power through a bidirectional coupler. The picked-up power values are represented by the bidirectional coupler in voltage form, so the presented values will be the forward $V_F$ and reflected $V_R$ voltages.

The measured $V_F$ and $V_R$ voltages are then combined together by special equations (mathematical formulas) to produce a nominal calculated value. This value will reflect in one way or another the real match level.

Voltage Standing Wave Ratio (VSWR) is the most common expression to indicate the degree of match:

$$VSWR=(V_F+V_R)/(V_F-V_R) \quad (1)$$

Also there are other widely used expressions, which demonstrate the actual match level. These expressions are the reflection coefficient ($\rho$) and the return loss coefficient, and many more.

When a stable power RF generator is used to transmit EM-energy at a stable load (media), and where the RF generator output impedance and the load impedance have almost identical values, then the resulting level of match will also be stable. When the load (media) or a part of it moves within the transmitted EM-field, then the total resultant characteristic impedance of the load will vary positively or negatively, this move will also vary the match level, according to how the match or mismatch occurs.

The method of the present invention can be precisely described as follows:

Stable EM-energy is applied to a scrutinized media containing the inspected target by a balanced type antenna. The EM-current flow within the said media at specific frequency will indicate the total complex characteristic impedance of the media.

A matching network will examine the total resultant complex characteristic impedance of the media, and will produce a buffered real impedance (resistance) value percentagely adjusted to match the transmission-line impedance connected at its input. By applying the basics of transmission line concepts (See "The American Radio Relay League Handbook," 76th edition, pages 19–3 (1999)), the generated EM-energy is divided within the transmission line into two parts—one part is the "forward" or "incident power," which travels outwardly along the line from the source until it reaches the load (inspected media), where it is then completely absorbed due to the match status. The other part is the "reflected power," which is energy reaching the end of the transmission line (matching network input), and is reflected back toward the source that is due to the mismatch status.

The bidirectional coupler is used to instantly sample the two power values within the transmission line, where it detects the forward power before it is transmitted, and the reflected power, which is not released at all from the transmission line (closed system). These two power values are generally free from any ambient electrical interference or noises because the forward wave is sampled before it is transmitted and the reflected wave that has never been transmitted or released from the said transmission-line. That is why amplifying the extracted impedance match variations is safely applicable to great gain levels (few million times). However the system sensitivity and stability mainly depends on the design quality of the device in addition to the mechanical stability of the inspected media.

Various prior art has adapted radar techniques to detect minute body movements by transmitting ultrasound, light, laser, or EM-waves to the target of interest. Through measuring the time-delay or the shift in the phase/frequency (Doppler effect) of the return waves reflected back from the surface of the target, the target movements are detected.

The patent to Geiger, U.S. Pat. No. 6,150,941, discloses a method for noninvasive baby monitoring based on radar techniques, which is achieved by transmitting ultrasonic waves towards the target of interest and picking up the echo return by a microphone. The patent to Corn, U.S. Pat. No. 6,062,216, discloses a similar detection system but utilizes a laser beam. The patents to Allen, U.S. Pat. No. 4,085,740, and to Sharpe, U.S. Pat. No. 4,958,638, both disclose a similar detector, but utilizing EM-waves.

Many other patents suggested the exploiting of parasitic effects of the target on the antenna impedance, such as by utilizing near field or dielectric resonator effects. In this matter the patent to Wolff, U.S. Pat. No. 5,670,886, which is based on the near field effect, is intended for detecting the movements of metallic-type activated targets. This is achieved by electromagnetically charging the metallic surface of the target through directing EM-waves toward the subjected surface, due to what is the so-called virtual capacitance, which occurs between antenna and target surfaces. The feedback of the opposite-polarity charged object would affect the antenna impedance. This is influenced by the reflected waves from the target.

The method of Wolff is intended for detecting metallic-type, nonconcealed objects in close proximity (a few millimeters). This is due to the limitations of the near field effect.

The patent to Boyko, U.S. Pat. No. 3,599,197, discloses a method for detecting moving objects based on coaxial line resonator capacitatively coupling a radiator to comprise an active antenna. The impedance variation of the radiating antenna will influence the center frequency of the previously tuned cavity resonator, which then influences the selectivity of the receiving circuit.

The present invention has many advantages over all the prior arts. It has much higher sensitivity over a wider range of ambient conditions, and additionally concealed metallic and nonmetallic objects are detectable at greater distances. Also, the chosen frequencies utilized by prior art are found in ultra-high ranges, such as high microwave and UHF bands, which are subject to parasitic behavior, which is clearly a disadvantage in circuitry design.

The prior art has no flexibility over the geometry or size of the transmitting antennas.

It is a specific object of the present invention to provide a concealed, moving-object detection system in which the actual total complex characteristic impedance of the inspected media is examined directly (nonreactively) by the output buffering stage (matching network).

It is another object of the present invention to track the target movements by monitoring the resulting forward and reflected waves, which are free from ambient interference and noises. The resulting waves basically occur on the basis of the transmission line impedance match and mismatch concepts. Moreover the monitored waves are sampled before being released from the transmission line.

It is still another object of the present invention to provide an interfacing buffer stage between the monitoring circuits and the real free space. This is achieved by the use of the matching network to match the impedances of the RF transmitter/transmission line with the scrutinized media. In addition, and due to its structure, it acts as a harmonic reject filter, which is based on inductive-capacitive (LC) type circuits, from any of the T-, L-, or Pi-type filter networks.

The present invention can be considered as a closed system due to the absence of any receiving mechanism, which increases the sensitivity to extremely high levels. However, practical observations of the primary prototype device proved that it was possible to detect through a cement wall slight movements of the human finger at a distance longer than a meter.

Considering the present invention as a closed system will make it very difficult to effect intrusion into the area under scrutiny, without initiating the system. This is a basic essential to any compact security systems.

The proposed invention, as an example, can be used to detect the infestation by stem borers, which attack deep inside the tree trunk. This can be achieved through creating a stable EM-field around the tree trunk by a balanced-type, encircling antenna.

Then the complex impedance structure of the tree trunk matches the transmitter output impedance through a matching network. The EM-energy passes through a bidirectional coupler, which produces the $V_F$ and $V_R$ signals. By the use of DC-blocking capacitors (High Pass Filters-HPF), the variable values which indicates the movement parts of the load from the resultant $V_F$ and $V_R$ will pass only through these capacitors.

These quite small variable signals are then directed to a linear circuit called an equation processor, which combines both variable signals by utilizing the selected equation, e.g., loss coefficient ($V_R/V_F$), or others.

The output signal from the equation processor then can be greatly amplified to a level where it can drive a visual or audio alarm indicator. The same general method described above can similarly be adapted to achieve all the applications aforementioned.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2a illustrates a cross-section top view of the tree trunk surrounded by the transmitting antenna assembly.

FIG. 2b illustrates the side view of a cross-section top view of the tree trunk surrounded by the transmitting antenna assembly.

FIG. 2c illustrates the components of the preferred transmitting antenna assembly.

FIG. 3a illustrates the preferred position of the patient antenna, which can be placed in front or in back of the patient. Also, two electrodes or metal sheets can be used as an antenna to surround the human chest (heart side), one from back, another one from front.

FIG. 3b illustrates a top view of the overlapped conductors used as transmitting antenna.

FIG. 3c illustrates the assembly details of the preferred transmitting antenna.

FIG. 4a illustrates the position of the transmitting assembly, which could be placed on the underside of a baby's bed or an infant incubator. The transmitter block used here is similar to the one used in FIG. 3.

FIGS. 4b and 4c show another two alternative arrangements for the transmitting antenna.

FIG. 7 illustrates an embodiment of the invention in the automatic access control. Such an arrangement can be used to control sliding doors 46. To eliminate the interference that will occur due to the natural automatic door closing process, doors can be made from nonmetallic material. Alternatively, the door closing speed can be adjusted to be outside of the device-responding bandwidth.

DETAILED DESCRIPTION OF THE PREFERRED EMBODIMENT

In the drawings:

1 is an RF transmitter;

2 is a bidirectional coupler;

3 is an antenna tuner (matching network);

4 is an output transmitting cable;

5 is an unbalanced-to-balanced transformer;

6, 26, 31, 32, 38, 39, 40, 42, 44, 45, 47, 49, 52, and 53 are various types of transmitting antennas;

7 and 16 are RF and linear grounds, respectively;

8 is a suspected tree trunk;

9 is a targeted pest;

10 and 11 are forward $V_F$ and reflected $V_R$ voltages, respectively;

12, 14, 13, and 15 are the RC high pass filters (HPF);

17 and 18 are the extracted variable signals from the basic $V_F$ and $V_R$ voltages;

19 is an equation processor block;

20 is an O/P signal $V_E$ from the equation processor block;

21 is a preamplifier and filter circuit;

22 is a signal carrier extension cable;

23 is an auto gain ranging amplifier;

24 is a final indication (driving) signal;

25 is a monitoring and alerting indicator;

27 is a tighten rubber;

28 is a coaxial cable;

29 and 36 indicate a human body;

30 is a transmitter assembly;

33 is an insulator housing;

34 is an electromagnetic field;
35 is a patient's heart;
37 is a baby's bed or incubator;
41 is a landscape area under security protection;
43 is a security device;
46 is a sliding door;
48 is corridor walls;
49 is a liquid-flow transducer assembly;
50 is a nonmetallic tube;
51 is an inspected liquid;
54 is an insulated and shielded transmitting wire;
55 is an area under inspection/corridor;
56 is an RF tank inside the bidirectional coupler;
57 is a circuit for achieving a symmetrical bidirectional coupler;
58 is a negative DC voltage generator;
59 is a Velcro type binding;
60 and 61 are RF form forward $V_F$ and reflected $V_R$ voltages, respectively;
62 and 63 are DC blocking (AC coupling) capacitors;
64 and 65 are rectifying diodes;
66 and 67 are demodulated signals;
68, 73, 74, and 77 are RF suppression chokes;
69 and 70 are the demodulating (integrating) capacitors;
71 is a deference amplifier;
72 is an O/P of deference amplifier;
75 and 76 are integrating resistors; and
78 is the reactive transmission-line.

The device structure according to the invention, for all the applications aforementioned, has generally the same configuration. The slight difference in specification between each individual application is due to the difference in the requirements from one application to another. These differences will be explained in the related sections.

Figure 1:
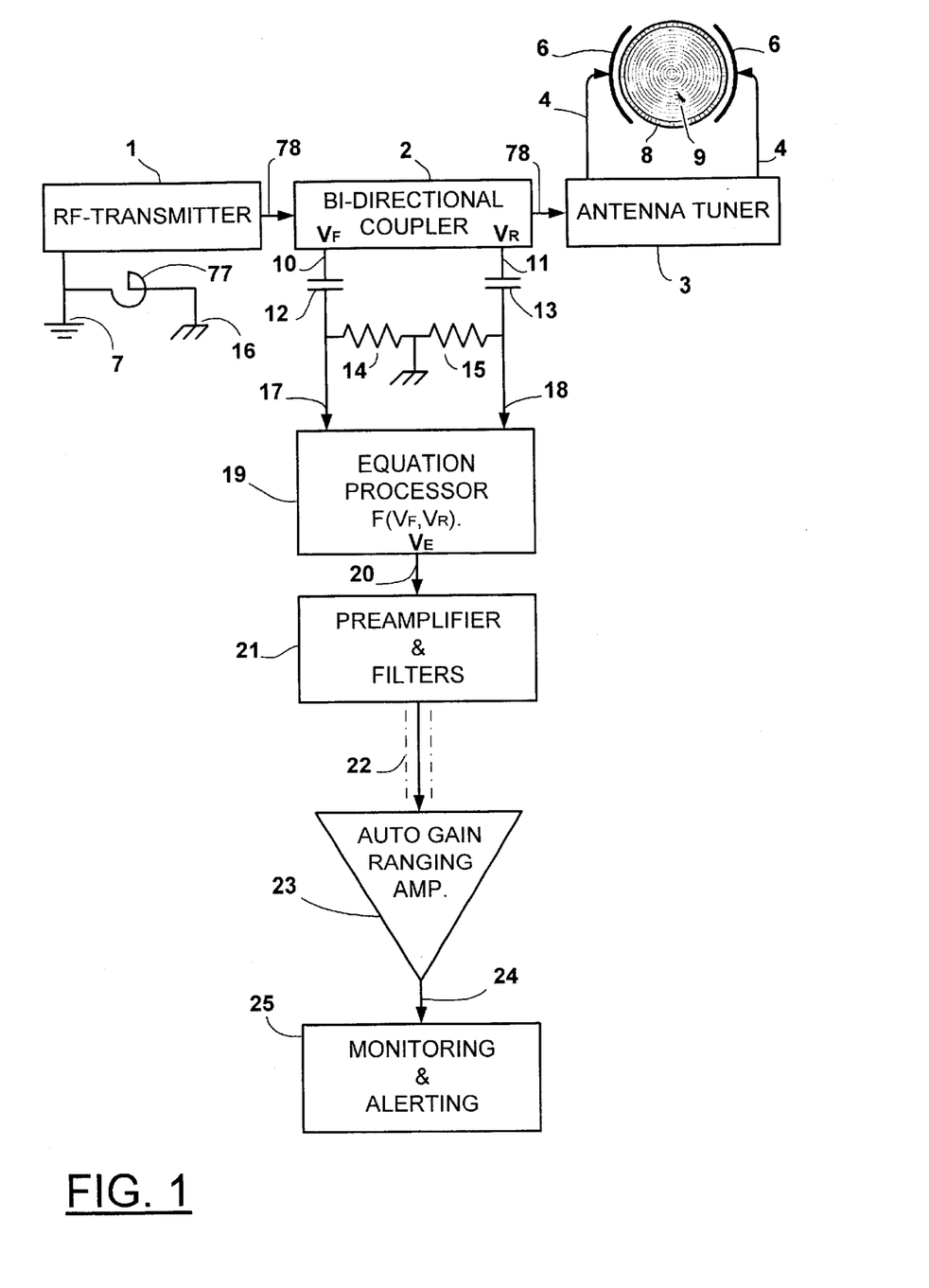
FIG. 1 illustrates the general block diagram of the preferred embodiment of the invention.
Figure 3:
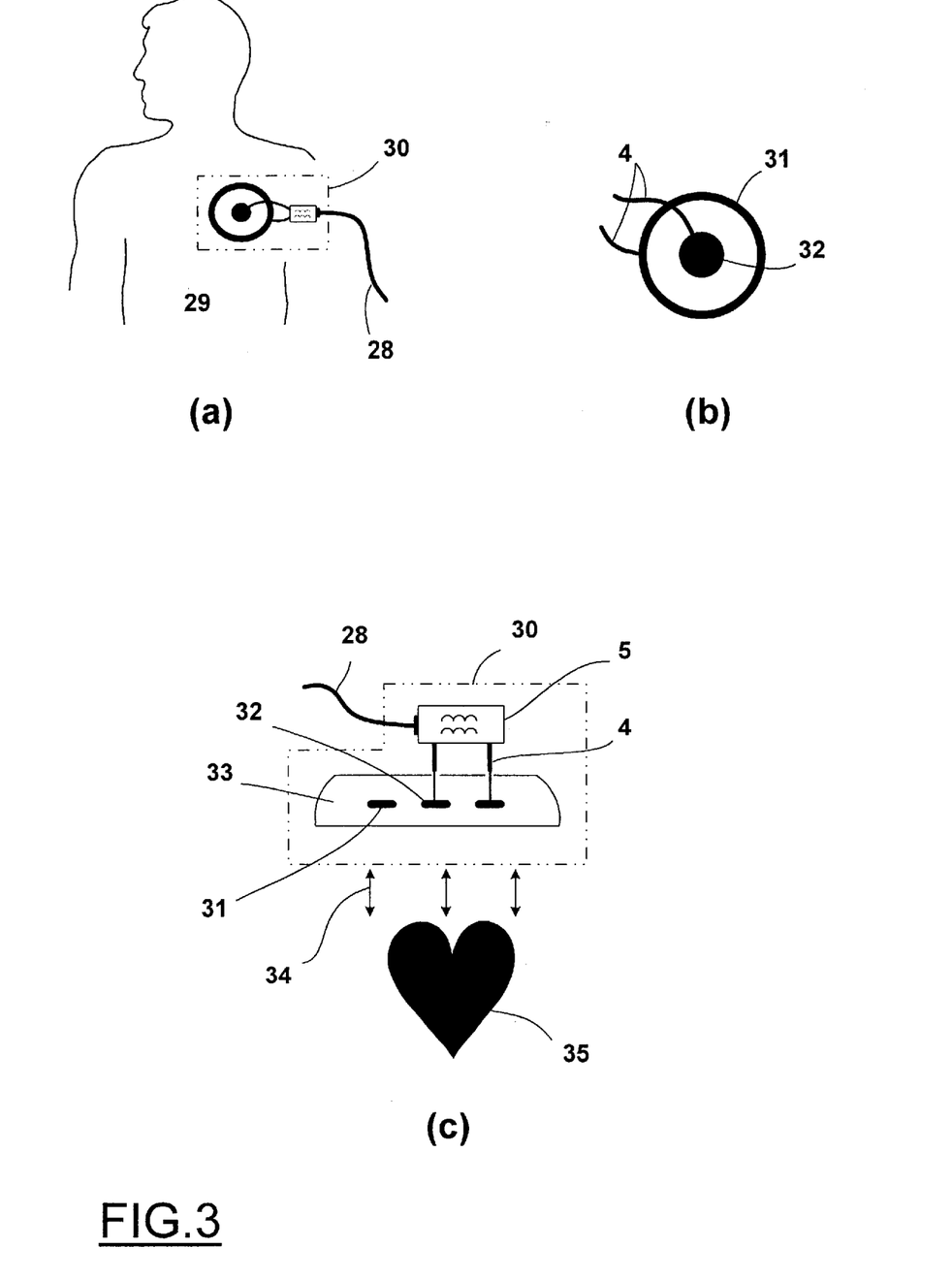
FIG. 3 illustrates an embodiment of the invention for use in the medical field for monitoring the motions of the human heart (kinetocardiograph).
Figure 4:
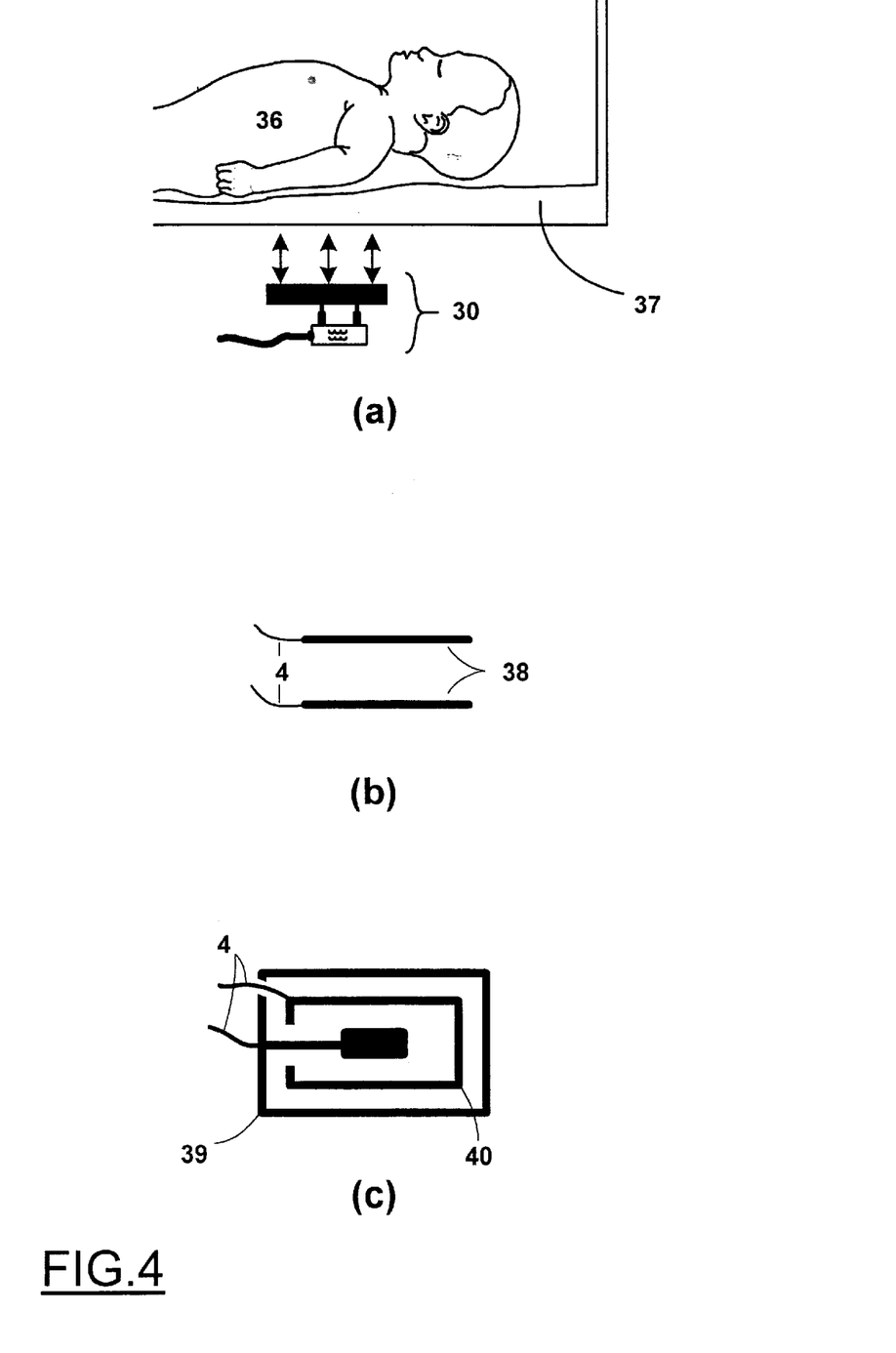
FIG. 4 illustrates another embodiment of the invention in the medical field for early detection of the threat of Sudden Infant Death Syndrome (SIDS).
Figure 5:
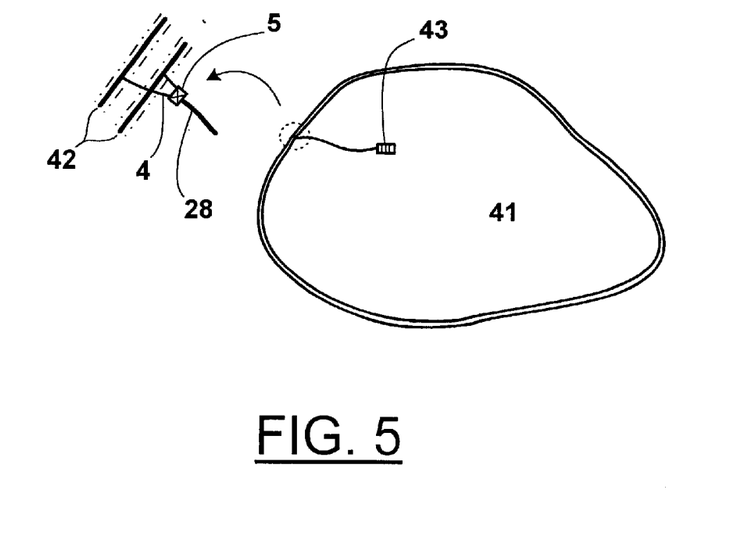
FIG. 5 illustrates an embodiment of the invention in a concealed security system. Here, two parallel insulated wires 42, positioned underground, are used to encircle the landscape 41 under scrutiny.
Figure 6:
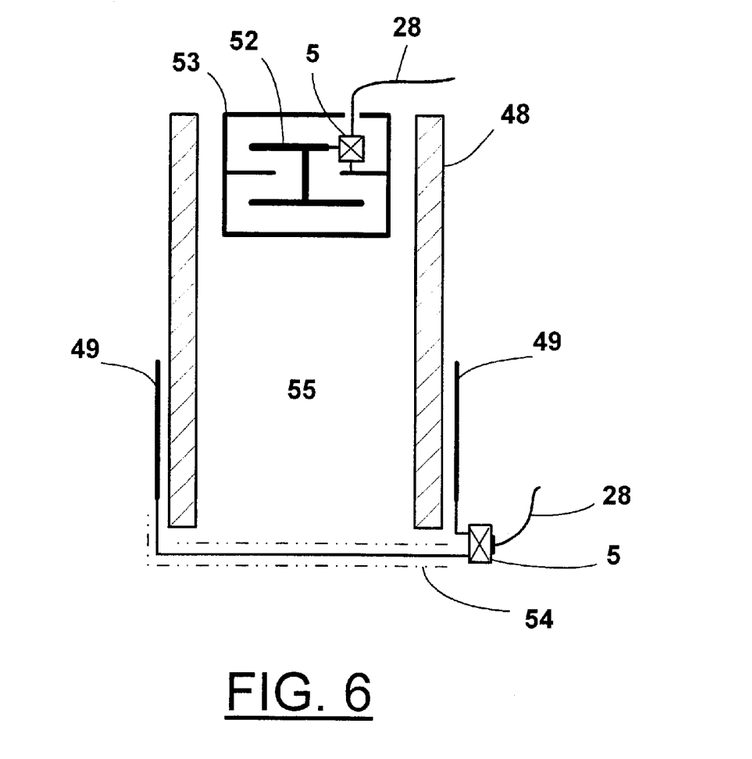
FIG. 6 shows another embodiment of the invention in concealed security applications for the use in closed areas like in corridors 55. The transmitting antennas can be placed underground 52, 53 or behind 49 the walls 48.

Referring to the drawings, and more particularly to FIG. 1, the first part of the device is the generator of the EM-waves. This is an RF transmitter 1 with a power level from a fraction of one watt to a few watts. The power has to be minimized for more safety in case of applications related to the human body, such as in cardiographs (FIG. 3) and for newborn babies (FIG. 4). This is also applicable in cases where there is a need for the use of nonstandard frequencies, which are not permitted. The frequency of the RF transmitter 1 should be tuned to match as near as possible the resonance frequency of the targeted objects 9, 35. In general, utilization of the standard permitted frequencies; e.g., 27.12 MHz, in such applications is adequate and satisfies the requirements.

The generated RF energy passes through a bidirectional coupler 2, which detects and identifies the actual values for the $V_F$ 10 and $V_R$ 11 signals. Then the RF energy is directed to the matching network or, more precisely, to what is the so-called antenna tuner 3. The function of the antenna tuner is to convert the complex parasitic impedance of the load (media) structures (i.e., human body 29, 36, tree trunk 8, etc.) into a real impedance value and to match, as closely as possible, the output impedance of the RF transmitter 1.

In certain applications, the need of high-speed automatic-type antenna tuners is essential in comparison with manual or semi-automated tuners. The applications that require the use of a high-speed antenna tuner with tuning time of a few seconds or less are those in which the time is limited. For example, in heart monitoring (FIG. 3), it is necessary to minimize the device preset time as the full process of cardiograph monitoring is executed within the time frame occurring between breath cycles. This is to isolate the heart activity from lung motion so as to obtain a few full cycles of the heart's activity in between the volitional breath pauses. Additionally, the device can be tuned to identify the heart movement in isolation to the lung activity by narrowing the time response bandwidth. This is because lung activity is much slower than heart movement, where a patient can voluntarily slow down or even can stop his breathing process for a few seconds.

Using an antenna tuner of the so-called unbalanced-output type enables the use of a single transmitting cable. This cable is connected to a single conductive rigid or flexible metal plate, which can have any geometric form or size. A metallic grille, grid, rod, or even just a wire may be used in place of the metal plates to function as a transmitting antenna. In a few applications, the transmitting antenna, wherever possible, should encircle the load media, for example, a tree trunk 8 when the device is intended to detect the infestation by pests 9.

When a balanced-output type antenna tuner 3 is used or when an unbalanced-type antenna tuner is connected to the input of the unbalanced-to-balanced transformer 5 (FIG. 3), it will enable the use of dual transmitting cables 4 together with dual (balanced) transmitting antenna 6, 31, 32, etc., so as to narrow the detecting and monitoring area. Each of the antennas could have the same aforementioned configuration described. Then, using adjacent, opposite, or encircling dual-transmitting antenna 6, 31, 32, etc., on the targeted load 8, 29, 36, sensitivity will be increased. This will result in the narrowing and direction of the EM-field 34 FIG. 3) to cover mainly the targeted area.

The output $V_F$ 10 and $V_R$ 11 signals produced by the bi-directional coupler 2 pass through a so-called a high pass filter (HPF) consisting of, in its simplest form, an AC coupling (DC blocking) capacitor 12, 13 in series, with a resistor 14, 15 in parallel. This will pass only the required variable $V_F$ 17 and $V_R$ 18 signals (FIGS. 1 and 9), which have the indication for any movement in the load (media).

Variable $V_F$ 17 and $V_R$ 18 signals then pass to the analog equation processor unit 19, which then uses the preferred arithmetic equation (formula) to combine the $V_F$ 17 and $V_R$ 18 signals. This then produces a signal $V_E$ 20, where $V_E = F(V_F, V_R)$. As an example and not by way of limitation, equations such as VSWR or the reflection coefficient, etc., can be achieved by the use of analog circuits.

The analog equation for the VSWR, $V_E = VSWR = (V_F + V_R)/(V_F - V_R)$, can be achieved by using an analog summing amplifier to function as its nominator ($V_F + V_R$), and an analog difference amplifier to function as its denominator ($V_F - V_R$). Then the value of VSWR is achieved by dividing the resultant values for the nominator by the denominator. The division can be carried out by the use of analog logarithmic and anti-logarithmic circuits, or by using ready made analog dividing integrated circuits (IC). For example, the analog divider IC "AD538" made by Analog Device, Inc., or similar ICs made by others, are suitable. In similar ways, it is easy to utilize the analog circuits to realize the equation for the reflection coefficient:

$$V_E \rho = (V_R/V_F), \text{ or its opposite value } 1/\rho = (V_F/V_R) \quad (2)$$

Selection of any one from the given equations is dependent upon the final design requirements. Utilizing the VSWR equation gives more stability over a wide range of noise and drifts, etc., which are produced in the RF transmitter 1. Where such noise effects will modulate the RF EM-waves, such modulation theoretically will not result in any change in the VSWR value.

Figure 7:
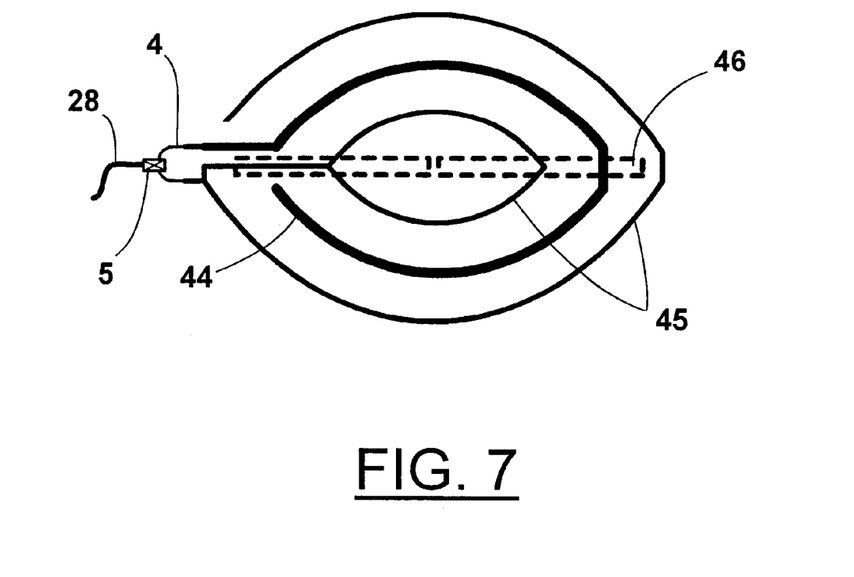
Figure 8:
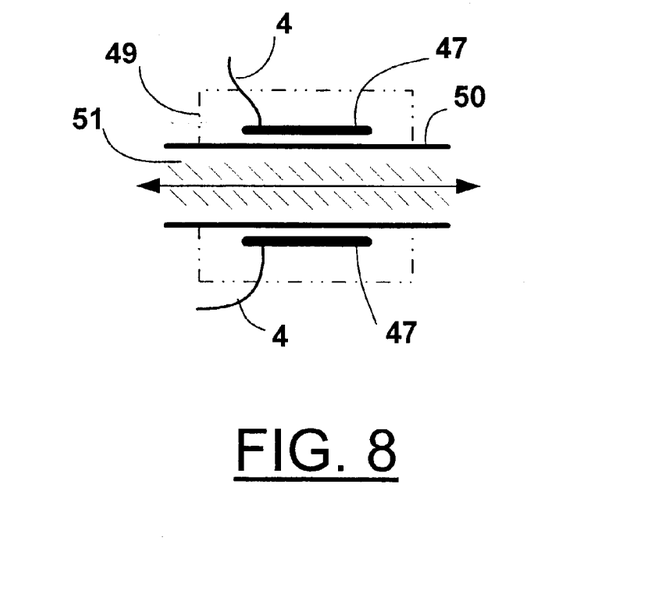
FIG. 8 illustrates an embodiment of the invention for sensing any fluctuation in the flow of liquids 51 in nonmetallic tubes or piping 55.

Normally, due to the use of a large number of components to achieve the VSWR equation circuit, the resulting internal components' noise is added to the requested useful signal. Therefore the use of VSWR formula is preferable in applications such as the access controls (FIG. 7) and cardiography (FIG. 3), wherein size of the targeted object 35 is relatively large and high stability and low gain (few thousands) is desired.

When the VSWR equation is used, $V_F$ 10 and $V_R$ 11 signals should pass directly to the equation processor unit 19. This eliminates the need for the HPF 12, 13, 14, 15 in the input circuit, and the HPF should be located at the output of the equation processor. This configuration can be applied also to any dividing equation.

Other equations like ($V_F/V_R$) or ($V_R/V_F$) dramatically improve the device performance, because it uses fewer components in comparison to the VSWR equation, so it gives improved results and stability over a wider range of conditions.

Analog circuits also can achieve the non-standard and useful equations, such as ($V_F-V_R$) or ($V_R-V_F$). These subtractive equations enhance the performance over a wide range of conditions. This is due to the use of so-called difference type or instrumentation amplifier (IA). Where IA has a very high common mode rejection ratio (CMRR), this enables operation in a noisy environments. Various IA ICs, which have ultra low internal noise of about 1 nv are available and are produced widely by many manufacturers, such as IA IC "INA103" made by BURR BROUN, Inc.

Satisfactory results can be achieved by using only one of $V_F$ 17 or $V_R$ 18 signals, especially where an application does not require a very high gain or if high quality and less noisy components are utilized in a perfect design, and if the system is used in an area of low interference and ambient noise.

Practical observation has shown that the variable components 17, 18 of the $V_F$ 10 and $V_R$ 11 voltages, which are generated by the moving objects within the scrutinized media, have an approximately symmetric nonproportional relationship. This is especially achieved when a good degree of match is reached. This means that when the $V_F$ 17 signal increases, the $V_R$ 18 signal decreases and vice versa, a combined differential signal occurs.

This conclusion represents the variable components of the $V_F$ 10 and $V_R$ 11 as a source of differential signal. This highly improves the use of subtracting equations ($V_F-V_R$) or ($V_R-V_F$). Where IA can perfectly achieve such equations, this type of amplifier is specially designed to work with the differential-type signal to provide a higher performance over a wide range of unstable ambient conditions.

Figure 9:
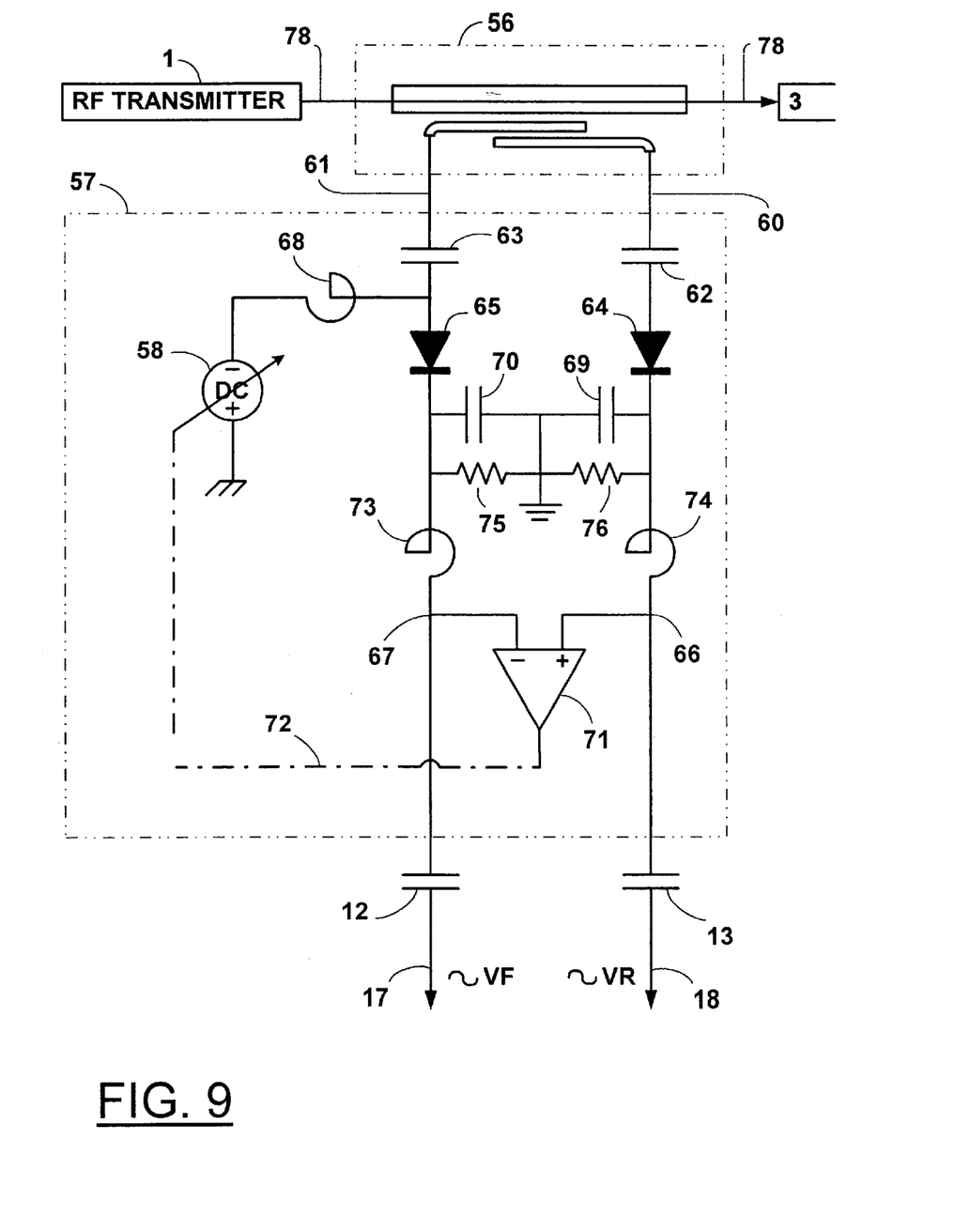
FIG. 9 illustrates the general block diagram for achieving a good level of linear symmetry for the rectifier diodes of the bidirectional coupler. The RF pickup coils 56 sample the basic $V_F$ and $V_R$ HF voltages, then the pickup signals pass to the demodulator (rectifying) stage 57. The difference amplifier 71 produces a signal to control the source of the negative DC voltage 58 until the output voltage of the difference amplifier 72 reaches zero.

Normally, when a good degree of match is reached, the final $V_F$ 10 signal becomes greatly larger than the $V_R$ 11 signal. This reduces the symmetry between the variable $V_F$ 17 and $V_R$ 18 signals. This happens due to the different working (saturation) points at the nonlinear (exponential) Volt-Ampere Characteristic (VAC) of the rectifying diodes. Normally, these diodes contained in the bidirectional coupler 2, which is used to detect the $V_F$ 10 and $V_R$ 11, signals in the RF tank 56 (FIG. 9).

The use of a so-called active diode, where a silicon passive diode is fixed in the feedback circuit of an operational amplifier, will help, but it is still not enough, as such high frequency operational amplifiers generally produce a relatively high level of internal noise.

Still, there is a need to find other effective ways to deal with this problem. An excellent alternative way (FIG. 9) can be achieved by shifting down the positive voltage level of the RF signal 61 before it reaches the rectifying diode 65 of the $V_F$ detection circuit. In this way, both diodes 64, 65 will work in the same working (saturation) point at the VAC. This can be achieved by applying a negative DC voltage 56 at the $V_F$ diode anode 65. This equalizes the rectified DC voltages 66, 67 at the cathode of both diodes 64, 65. This way will not affect the requested variable signal 17, 18, as these signals are so small, and in the worst case they are greatly smaller than the RF form $V_F$ 61 and $V_R$ 60 signal, so by this way symmetry is achieved.

The $V_E$ 20 signal generated in the equation processor unit 19 as a function of $V_F$ 17 and $V_R$ 18, in accordance with the required and used equation, is then ready for the following processing steps.

The $V_E$ 20 signal needs to be amplified to that level where the analyzing and monitoring can be executed. In addition to the amplification, filtration will be required.

The $V_E$ 20 signal then passes to the amplifier circuits 21, 23, which contain multi-amplifier stages. In the preamplifier first stage circuit 21, the signal should have an acceptable gain level (few hundreds time). Then the main gain can be obtained by manual adjustment or by an auto gain ranging amplifier 23. The total gain range for the amplifiers should cover all the possible signal amplitude variations. This occurs due to the different sizes, positions, and structures of the inspected media or objects.

Signal filtration is a major part of the amplifier circuits 21, 23, which generally helps in minimizing the noise and interference that may reach the device circuits. The signal filtration is achieved by the introduction of passive and active, high- and low-pass, wideband, and notch filters wherever possible in the various stages of the device. The filters' bandwidths are defined according to the expected motion speed of the tracked targeted object 9, 35 etc.

The final stage 25 will be the provision of audio or visual indications of the monitored subject. This can include a hard copy of the observation results if required. Additionally as an example, visual indications can be complemented by the use of a buzzer with different tones or Light Emitting Diode (LED) to show the level of infestation by red palm weevil 9. This can be achieved by averaging the signal peaks for one insect in a defined period of time, then by counting the number of peaks within the same time interval. The combinations of manner of indicating the presence of the pest are manifold. Additionally, the resulted (indication) signal 24 can be used for analytical purposes in applications that require such analysis.

Device sensitivity can be changed by adjusting the amplifier 23 gain or by shifting the response level threshold. This detection circuit for the response threshold may be located in or before the final stage 25 where it is used to drive a variety of types of indicators, such as for triggering the alarm circuits.

Finally special care should be taken in fabrication and operation of the device in the real world. The device should be well screened and shielded—this is to minimize the external EM-interference or noise effects. These noise effects could originate from the air currents flowing inside the device. The assembly design should include a metallic separation partition in between the linear and the RF circuits.

Additionally the RF ground 7 and the linear circuit's ground 16 should be well RF-isolated. This can be achieved by joining both grounds through a suitable RF inductive suppression choke 68, 73, 74, 77 at a value range of a few milli-Henry.

Extra care should be taken to ensure that the operator is sufficiently remote from the detection area to be sure that there is no possibility of undue interference. This can be achieved by separating the device into two individual parts. One can include the circuits up to the preamplifier 21, the other to include all remaining circuits that will be directly used by the operator. This is to allow the operator to do the necessary tuning and adjustments. The link 22 between the two units should be sufficiently long and should utilize good shielded cable.

Figure 2:
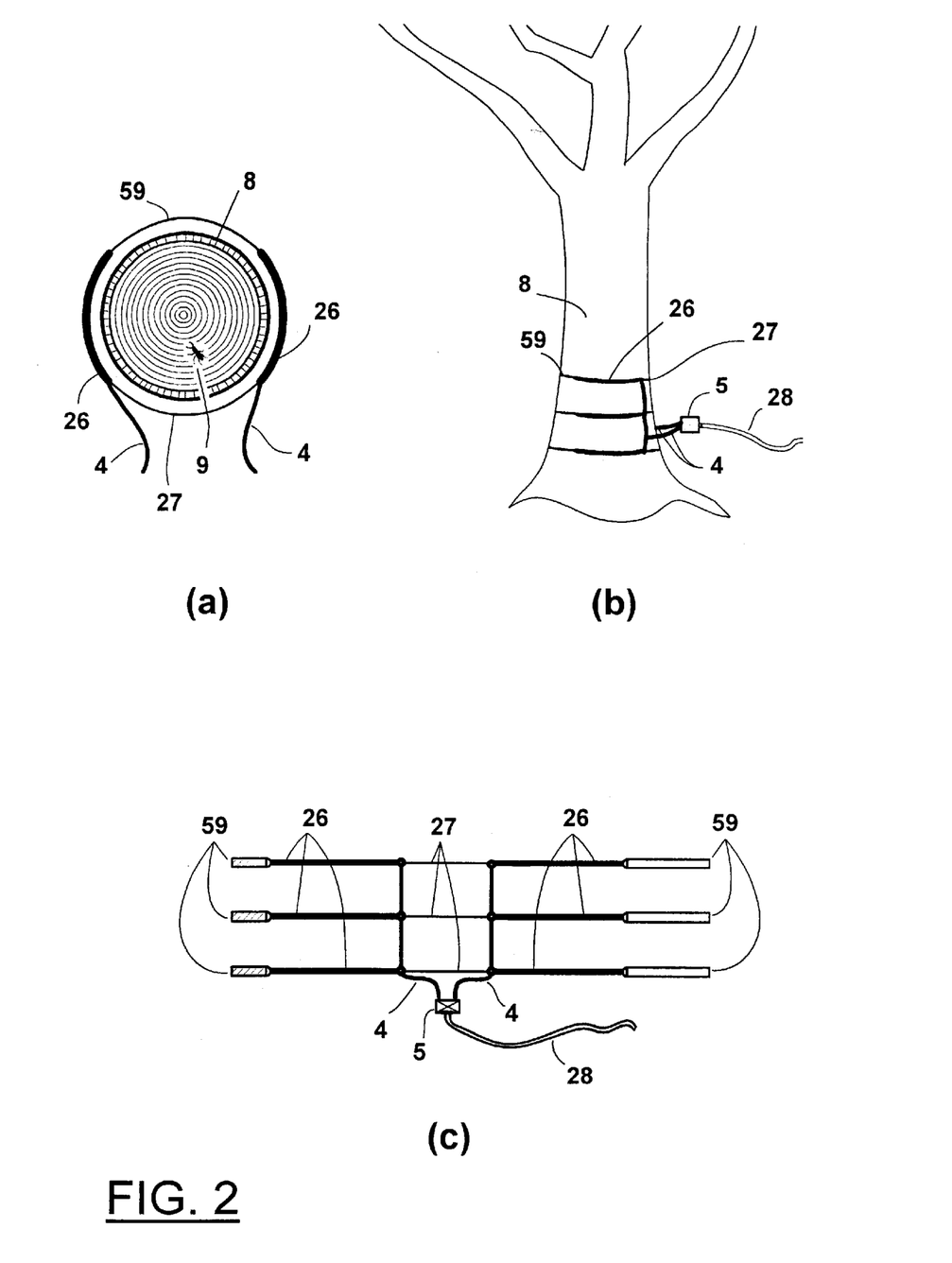
FIG. 2 illustrates an embodiment of the invention in the agriculture field for detecting the infestation by red palm weevil and stem borers hidden deeply within the tree trunk or the upper roots.

When the device is used in the open field, e.g., to detect the tree infestation (FIG. 2) by borer pests 9 hidden inside the tree trunk 8 or the upper roots, the total surface area of the transmitting antenna 26 should be minimized so as to eliminate the wind effect which could vibrate the antennas. Any vibration could generate an interference signal. To solve this, rubber 27 or Velcro®-type bindings 59 can be used to tighten the transmitting parallel wires 26 or springs onto the tree trunk 8.

Wherever it is considered necessary to have an extended transmitting cable and where the use of dual (balanced) transmitting antennas is preferable, this can be achieved by utilizing the unbalanced-type antenna tuner through connecting to unbalanced-to-balanced transformer 5 (FIGS. 2–7). This will enable the length of the transmitting cable to be extended by the use of high quality RF coaxial cable 28.

The surface areas of the transmitting cables or the antennas have to be electrically well insulated by the use of proper insulation 33 (FIG. 3), such as rubber, PVC, etc., especially when the working media contains a high volume of moisture or in the case of applications related to human bodies.

In security applications (FIGS. 5 and 6), as an example, the transmitted RF energy can be modulated with a medium range frequency (few kHz) to disable the possibility of any interference caused by intruders. Such modulation will require narrowband pass filters of the same modulating frequency in the device inputs' discriminating circuits.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. Apparatus for non-invasively detecting movement of object(s) and/or fluid flow in a body, said apparatus comprising:

radio frequency (RF) transmitter means for generating RF radiation;

at least one RF antenna for directing RF radiation generated by the said transmitter means to the body being monitored;

antenna tuner means for matching the output impedance of the said transmitter means with the equivalent impedance of the said body; and processor means for equationally processing the forward and reflected transmission-line voltages to provide an output signal representative of impedance match changes to the said body with the said transmitter, whereby to indicate movement of at least one object or fluid flow in the said body.

2. A method of non-invasively detecting movement of object(s) and/or fluid flow in a body; said method comprising the steps of:

directing radio frequency (RF) radiation to the said body being monitored by RF transmitter means;

matching the output impedance of the said transmitter means with the equivalent impedance of the said body; and equationally processing the forward and reflected transmission-line voltages to provide an output signal representative of impedance match changes to the said body with the said transmitter, whereby to indicate movement of at least one object or fluid flow in the said body.

3. A device comprising:

a radio frequency (RF) transmitter for generating EM-radiation for detecting and/or monitoring concealed moving object(s) and/or fluid flow in scrutinized media, the said transmitter having a power range from 0.1 to 10 watts;

means for selecting an RF transmitter frequency to substantially match the resonance frequency of the object(s) or fluid being monitored, the said frequency being in the range of 1 to 800 MHz;

at least one antenna comprising metal sheets or wires, the said antenna being adapted for location in the region of the media containing the object to be monitored;

an antenna tuner means having an imipedance matching means for matching the output impedance of the RF transmitter with the equivalent impedance of the inspected media;

means for processing the forward and/or reflected transmission-line voltages to provide a single voltage signal;

means for extracting variable signals from the forward and/or reflected transmission-line voltages to generate an indicating signal which provides an indication of movement of the targeted object or fluid flow within the inspected media;

band pass filter means for filtering the indication signals to limit the variation range to cover only an expected motion of the targeted object(s) or fluid flow; and amplifying means for amplifying the indication signal to a level that can drive an indicator circuit.

4. A device as claimed in claim 3, wherein said single voltage signal comprises the voltage standing wave ratio (VSVWR) of the forward (VF) and reflected (VR) transmission-line voltages, where VSWR=(VF+VR)/(VF−VR).

5. A device as claimed in claim 3, wherein said single voltage signal comprises the reflection coefficient (ρ) of the forward (VF) and reflected (VR) transmission-line voltages, where ρ=(VR/VF).

6. A device as claimed in claim 3, wherein said device is adapted for detection of early infestation by stem borers or red palm weevils or other pests in all types of trees, hidden deeply within the tree trunks or upper roots.

7. A device as claimed in claim 3, wherein said device is adapted for remotely and non-invasively detecting and monitoring human body movements and vital signs.

8. A device as claimed in claim 3, wherein said device is adapted for direct sensing of sudden fluctuation in the flow of liquids.

9. A device as claimed in claim 3, wherein said device is adapted for use in concealed security systems.

10. A device as claimed in claim 3, wherein said device is adapted for the use in automatic access control.

11. A method for detecting and/or monitoring concealed moving objects or fluid flow in scrutinized media by detecting high frequency impedance match variations with the said media at a fixed Radio frequency (RF) by means of a monitoring device; said method comprising:

surrounding the inspected media with a field of high frequency electromagnetic (EM) waves through at least one transmitting antenna comprising metallic sheets or wires and having a power of 0.1 to 10 Watts;

matching the output impedance of the said monitoring device; with the equivalent impedance of the inspected media;

selecting the frequency of the EM-waves to closely match the resonance frequency of the targeted moving object or fluid, in the range of 1 to 800 MHz;

extracting variable voltages from the forward and reflected transmission-line voltages; and equationally processing the said extracted variable voltages, to produce a signal, which indicates movement of the targeted object or fluid within the inspected media.

* * * * *

UNITED STATES PATENT AND TRADEMARK OFFICE
CERTIFICATE OF CORRECTION

PATENT NO.    : 6,359,597 B2
DATED         : March 19, 2002
INVENTOR(S)   : Y.M.T. Haj-Yousef It is certified that error appears in the above-identified patent and that said Letters Patent is hereby corrected as shown below:

Column 11,
Lines 64-65, "object (s)" should not break

Column 12,
Line 4, "imipedance" should read -- impedance --
Line 24, "(VSVWR)" should read -- (VSWR) --

Signed and Sealed this

Twenty-eighth Day of May, 2002

Attest:

Attesting Officer

JAMES E. ROGAN
*Director of the United States Patent and Trademark Office*